United States Patent [19]

Ajioka et al.

[11] Patent Number: 4,922,005
[45] Date of Patent: May 1, 1990

[54] PREPARATION PROCESS OF HEXAMETHYLENE

[75] Inventors: Masanobu Ajioka; Makoto Aiga; Masafumi Kataita; Akihiro Tamaki, all of Omuta, Japan

[73] Assignee: Mitsui Toatsu Chemicals, Incorporated, Tokyo, Japan

[21] Appl. No.: 797,457

[22] Filed: Nov. 13, 1985

[51] Int. Cl.$^5$ .......................................... C07C 119/04
[52] U.S. Cl. ................................................... 560/347
[58] Field of Search ................. 260/453 PH; 560/347

[56] References Cited

U.S. PATENT DOCUMENTS

| | | |
|---|---|---|
| 3,424,780 | 1/1969 | Sayigh . |
| 3,544,611 | 9/1970 | Michelet et al. . |
| 3,544,612 | 12/1970 | Alheritiere et al. .......... 260/453 PH |
| 3,960,916 | 6/1976 | Fuchs et al. ................. 260/453 RH |

FOREIGN PATENT DOCUMENTS 1146664  3/1969  United Kingdom .

Primary Examiner—Alan Siegel
Attorney, Agent, or Firm—Fisher, Christen & Sabol

[57] ABSTRACT

Hexamethylene diisocyanate (HDI) is prepared by introducing a hexamethylenediamine (HDA) solution and an equivalent amount or more of hydrogen chloride gas simultaneously into a turbulent zone in the vicinity of an agitating blade in an inert organic solvent held under agitation within a tank-shaped reactor and allowing them to undergo a successive salt-forming reaction so as to obtain a high-concentration slurry of hexamethylenediamine hydrochloride (HDA·HCl) and then reacting the slurry with phosgene. The phosgenation is effected by charging an HDA·HCl slurry of a high concentration, such as that obtained by the above process, into a tank-shaped reactor held under a pressure above the atmosphere pressure but below 5 kg/cm$^2$G and controlling the amount of phosgene, which is to be blown into the reactor, at a level 1–18 molar times per hour the total amount of HDA·HCl and HDI in the reaction mixture. In a preferred embodiment of the phosgenation, the phosgenation reaction is effected in a continuous two-step tank-shaped reactor while controlling the degree of conversion in the first step within 70–95%. This is a rationalized preparation process of hexamethylene diisocyanate since it requires a shorter overall phosgenation time.

1 Claim, 4 Drawing Sheets

PREPARATION PROCESS OF HEXAMETHYLENE

BACKGROUND OF THE INVENTION (1) Field of the Invention

This invention relates to a preparation process of hexamethylene diisocyanate (hereinafter abbreviated as "HDI" for the sake of brevity), and more specifically to a process for preparing HDI in accordance with the hexamethylenediamine hydrochloride (hereinafter abbreviated as "HDA.HCl" for the sake of brevity) process, in which HDI is advantageously obtained on an industrial scale by preparing HDA.HCl of a relatively high concentration and then reacting it with phosgene. HDI is used as a modifier for various products including non-yellowing coating formulations and its demand is progressively increasing in recent years.

(2) Prior Art of the Invention

HDI has heretofore been prepared by a one-step reaction or cold two-step process, in which hexamethylenediamine (hereinafter abbreviated as "HDA" for the sake of brevity) and phosgene are reacted directly to each other, or by a hydrochloride process in which HDA is first formed into an acid addition salt such as HDA.HCl and then phosgenating the same. Although the direct one-step reaction features shorter reaction time as a merit thereof, it is accompanied by a drawback that byproduct tar and chlorohexyl isocyanate (hereinafter abbreviated as "Cl-HI" for the sake of brevity) occur in large amounts. On the other hand, the occurrence of byproducts is suppressed in the hydrochloride process. The hydrochloride process is however accompanied by such drawbacks that the phosgenation reaction takes longer time and when the concentration of the starting amine is high upon preparation of HDA.HCl, the viscosity of the reaction mixture increases significantly in the course of the salt-forming reaction and HDA tends to remain unreacted, and when the reaction mixture is phosgenated, more byproducts such as urea, Cl-HI and the like are formed. Accordingly, the preparation of the hydrochloride is generally effected to obtain HDA.HCl at a concentration of about 10% or so and the phosgenation is usually conducted on HDA.HCl of such a concentration.

U.S. Patent Specification No. 3,424,780 discloses that in a reaction between HDA.HCl obtained in a usual manner and phosgene, the occurrence of byproducts can be successfully suppressed by using a solvent in a large amount as much as 20–30 times relative to HDA.HCl. It is however economical to use such a solvent as little as possible in view of the size of a reactor and the recovery of the solvent. In addition, British Patent Specification No. 1,146,664 discloses to prepare HDA.HCl efficiently by means of a falling-film salt-forming apparatus and then to phosgenate the salt. This process is however accompanied by a shortcoming that a special apparatus is indispensable for the salt-forming step.

It has also been reported, for example, in U.S. Patent Specification No. 3,544,611 that the reaction velocity may be increased, the reactants may be used at higher concentrations and the yield of the intended product may be improved, all, by the pressure phosgenation process. However, these reported processes are all concerned with direct phosgenation reactions, in which free HDA is used. The phosgenation reaction of free HDA proceeds faster than the hydrochloride process and more byproducts are formed as the concentrations of the reactants increase. With a view toward suppressing the occurrence of such byproducts, the phosgenation is effected under pressure. It is also disclosed in these specifications that the unreacted phosgene can be recovered with good efficiency when the reaction is conducted under pressure.

SUMMARY OF THE INVENTION

An object of this invention is to provide an improved industrial process for preparing HDI by converting HDA into its hydrochloride (HDA.HCl) and then reacting HDA.HCl with phosgene.

Another object of this invention is to provide a process for the preparation of HDA.HCl as a high-concentration slurry free of unreacted HDI and also a process for the effective phosgenation of an HDA.HCl slurry of a high concentration.

In a preparation process of HDA.HCl, the reaction between HDA and HCl is very fast. In such a routinely-employed process that HCl gas is caused to pass through a solution of HDA in an inert organic solvent, use of HDA at a high concentration results in an increase to the viscosity of the reaction mixture due to precipitated HDA.HCl, the agitation of the reaction mixture cannot be effected uniformly, and hence, unreacted HDA become more likely to remain.

The present inventors investigated changes in viscosity of a slurry during the salt-forming step. As a result, it was found that the viscosity becomes highest in the intermediary stage until the concentration of HCl becomes from ½ equivalent to equivalent relative to HDA and the viscosity drops to one half upon completion of the neutralization of HDA. On the basis of the above finding, it was also revealed that an HDA.HCl slurry of a concentration as high as 10% or even higher can be easily obtained even in a usual tank-shaped reactor if the salt-forming reaction is carried out by feeding an HDA solution and HCl simultaneously to a turbulent zone under high-speed agitation so as to allow HCl to exist always in an excess amount.

On the other hand, it has conventionally been known that in the reaction between HDA.HCl and phosgene, use of phosgene in an excess amount promotes the reaction and suppresses the occurrence of byproducts. However, the use of phosgene in such an excess amount develops a new problem with respect to the recovery of unreacted phosgene. In view of the liquefaction temperature of phosgene, its solubility to a solvent and the like, the recovery of phosgene may be facilitated if the reaction is conducted while maintaining the whole reaction system under elevated pressure. Through an investigation conducted by the present inventors, it was however uncovered that when the reaction between HDA.HCl and phosgene is effected under elevated pressure, more and more byproduct Cl-HI and tar occur as the reaction pressure goes up and use of phosgene in a large excess is indispensable for the suppression of occurrence of such byproducts. It is therefore important to choose a suitable degree of excess of phosgene and an appropriate reaction pressure in order to achieve efficient preparation of HDI having a low content of byproduced Cl-HI by the reaction between a high-concentration slurry of HDA.HCl and phosgene.

Based on the above-described findings, the objects of the present invention have been fulfilled in the following manner.

Namely, an HDA solution and an equivalent amount or more of hydrogen chloride gas are simultaneously introduced into a turbulent zone of an inert inorganic solvent in the vicinity of an agitating blade within a tank-shaped reactor so that they are allowed to undergo a successive salt-forming reaction to obtain a high-concentration slurry of HDA.HCl, which is then reacted with phosgene. In spite of the high concentration of HDA.HCl obtained in the above manner, the slurry is free of unreacted HDA and has a uniform and low viscosity and the slurry is hence easy to handle. When the slurry is continuously phosgenated subsequent to its preparation, HDI of a high concentration can be obtained with low contents of byproducts such as Cl-HI and tar.

Furthermore, it is possible to reduce the Cl-HI content and at the same time to facilitate the recovery of phosgene provided that upon phosgenation, an HDA.HCl slurry is charged into a multi-stage tank-shaped reactor maintained under a pressure above the atmospheric pressure but below 5 kg/cm$^2$G and its phosgenation is effected while controlling the amounts of phosgene, which is to be blown into the individual reaction tanks, at a level 1–18 molar times per hour the total amounts of HDA.HCl and HDI in the reaction mixtures within the corresponding reaction tanks.

It is also possible to shorten the overall time of the phosgenation reaction in the present invention, provided that upon effecting the phosgenation reaction, a continuous two-stage reaction tank is provided and the reaction is carried out while maintaining the conversion in the first step within 70–95%.

Effects of the process according to the present invention are indicated by FIG. 1, which pertains to a reaction conducted in two stages in accordance with the process of this invention. Namely, FIG. 1 is a diagrammatic illustration of the relations among the reaction pressure, the molar ratio of phosgene blown per hour to the total amount of HDA.HCl and formed HDI in the reaction mixture, the proportion (i.e., wt. % based on HDI) of Cl-HI produced in the reaction mixture and the yield of HDI when HDA.HCl was phosgenated at 140° C. for a retention time of 3.3 hours in a 20% slurry of HDA.HCl in o-chlorobenzene as a solvent.

It is envisaged from FIG. 1 that lower pressures are better with respect to the formation of Cl-HI and the yield of HDI and when a higher pressure is employed, phosgene has to be fed in a greater excess. Especially, the boiling point of Cl-HI is very close to that of HDI so that the purification of HDI is difficult. It is thus necessary to suppress the formation of Cl-HI as much as possible. When the reaction is carried out at an elevated pressure higher than 5 kg/cm$^2$G, it is indispensable to feed phosgene in a large excess. Thus, the reaction is conducted under a still higher pressure. Although use of such a higher pressure facilitates the separation of phosgene, the use of phosgene in such a large excess leads to a higher initial cost with respect to facilities for the recovery step upon practice of the process on an industrial scale.

The present inventors have also found that the yield of Cl-HI decreases gradually in proportion to the pressure below 5 kg/cm$^2$G, especially, below 3 kg/cm$^2$G but when the reaction is conducted under slightly-elevated pressure, still greater effects can be brought about because the liquefaction temperature of phosgene is above room temperature at 1 kg/cm$^2$G or higher and the recovery of phosgene is rendered significantly easier at such slightly-elevated pressure compared with its recovery under normal pressure.

It is therefore possible to lower the Cl-HI content and at the same time to facilitate the separation of phosgene by conducting the phosgenation reaction while choosing a pressure within a specific range and at the same time, in accordance with the thus-chosen pressure, making a suitable adjustment to the flow rate of phosgene to be blown into the reaction tank.

DETAILED DESCRIPTION OF THE INVENTION

As inert inorganic solvents useful in the practice of this invention, may be mentioned those employed for the phosgenation of usual amines, for example, toluene, xylene, monochlorobenzene, o-dichlorobenzene (ODCB), trichlorobenzene, tetrahydrofuran, tetralin, amylbenzene and so on. Among these solvents, o-dichlorobenzene is particularly preferred. In the salt-forming step for HDA, the solvent may be used in an amount 5–16 times or preferably 6–10 times, both relative to HDA. If the solvent is used in a large amount, a large reactor is required and a great heat quantity is also required for the recovery of the solvent. If the solvent is used in any amounts smaller than the lower limit, the viscosity of the resulting slurry of HDA.HCl becomes so high that the slurry cannot be stirred or transferred in a usual manner.

As the amount of hydrogen chloride to be used in the salt-forming reaction, it may theoretically be sufficient if it is used in an amount required for the neutralization of HDA, in other words, in an amount twice the number of moles of HDA, namely, in an amount 2 molar times HDA. If HCl gas is blown into an HDA solution as in the conventional process, unneutralized portions remain locally even if the agitation is effected thoroughly. Thus, the viscosity of the reaction mixture increases. It is thus necessary in the present invention to feed an HDA solution and HCl simultaneously to subject them continuously to a successive reaction while using the HCl in an amount at least equivalent to the HDA and always maintaining the reaction mixture in an acidic state. The reaction is effected while blowing HCl gas at a temperature around room temperature and controlling the temperature of the reaction mixture below 150° C. The upper limit of the amount of HCl to be fed is 3 molar times. The preferred amount of HCl to be fed is somewhat more than 2 molar times. It is uneconomical to blow HCl in any amount greater than the upper limit, since such an extra portion of HCl merely passes through the reaction mixture.

Figure 1:
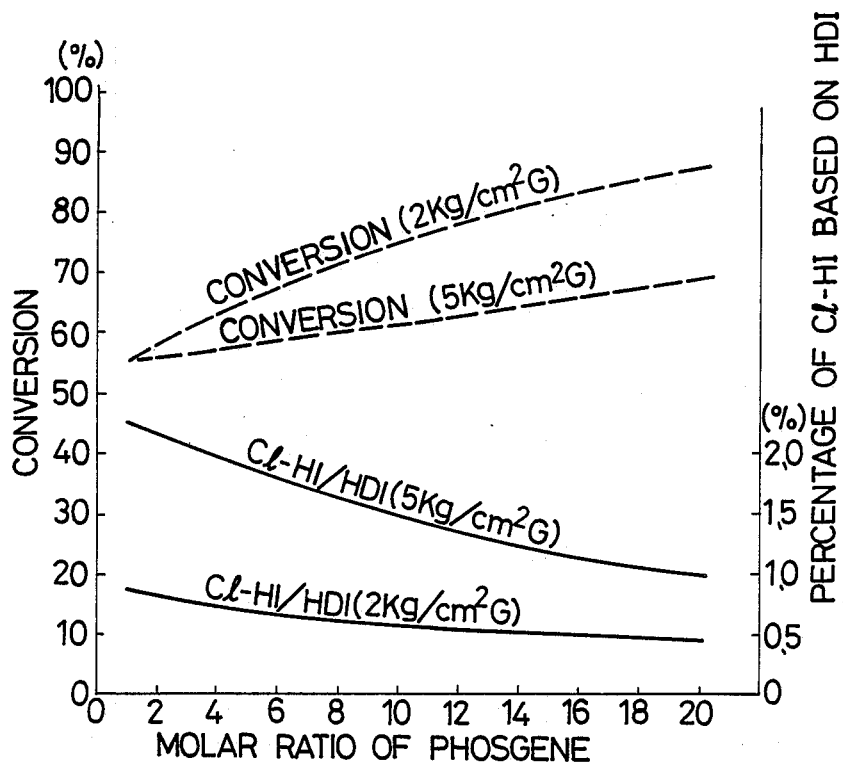
FIG. 1 is a diagrammatic illustration of the relations among the reaction pressure, the molar ratio of phosgene blown per hour to the total amount of HDA.HCl and formed HDI in the reaction mixture, the proportion of Cl-HI produced in the reaction mixture and the yield of HDI when HDA.HCl was phosgenated at 140° C. for a retention time of 3.3 hours in a 20% slurry of HDA.HCl in o-chlorobenzene as a solvent in the first stage of the two-stage phosgenation reaction according to the process of this invention.
Figure 2:
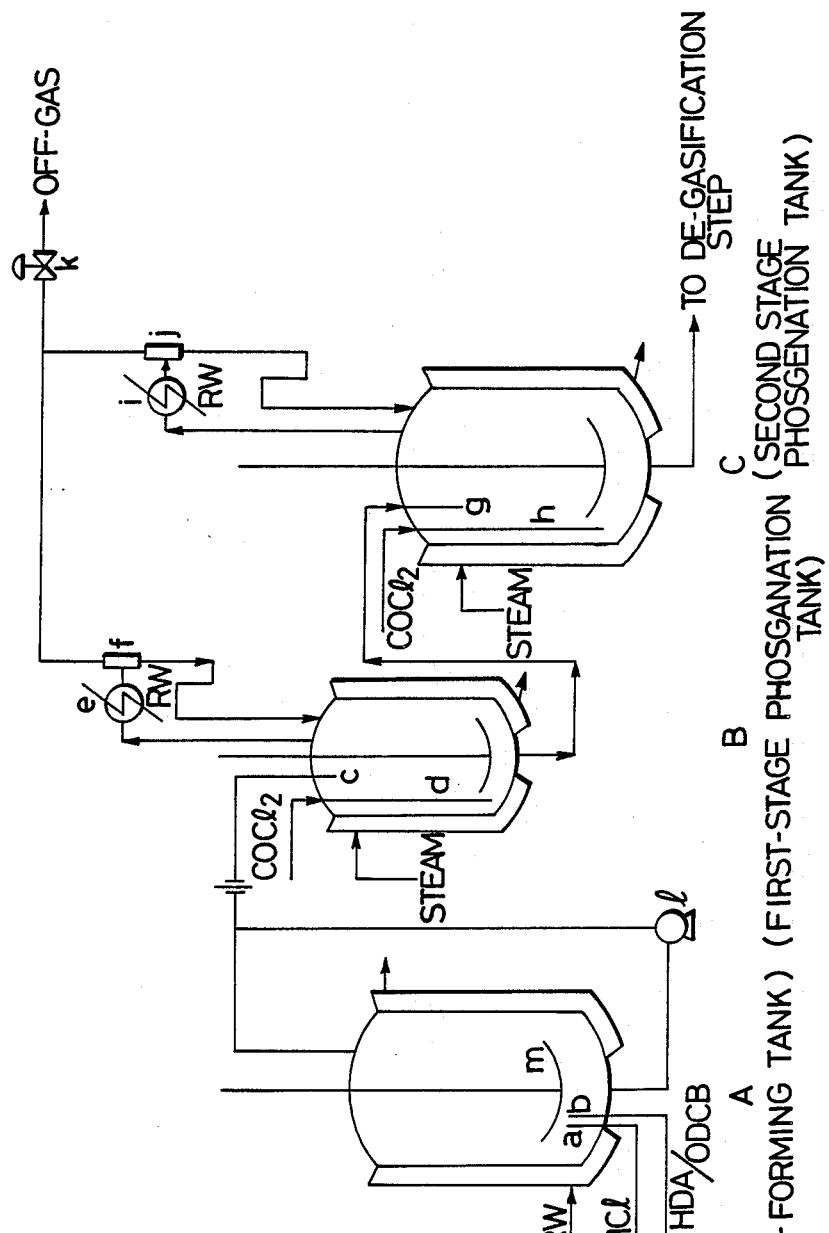
FIG. 2 is an illustrative flow sheet suitable for use in continuously phosgenating HDA.HCl in the process of this invention.

Although the subsequent phosgenation reaction may be carried out batchwise, the batchwise reaction is difficult to achieve uniform agitation when the concentration of the slurry is high. This insufficient agitation results in the formation of byproducts due to localized overheating and reaction and at the same time, renders the handling of the slurry difficult. When the phosgenation reaction is carried out batchwise, it is preferred for the above-mentioned reasons to subject HDA.HCl to phosgenation after diluting the HDA.HCl slurry with an inert solvent to a concentration of 10% or so as in the conventional process. When the HDA.HCl slurry is subjected continuously to the phosgenation reaction on the other hand, the agitation and mixing are facilitated. The continuous phosgenation reaction is also advantageous from the standpoint of phosgene recovery and process automation. It is thus preferred to subject the HDA.HCl slurry, which has been obtained in the preceding step, continuously to the phosgenation reaction. One embodiment of the continuous phosgenation reaction is illustrated by way of example in FIG. 2, in which the apparatus for synthetically preparing HDA.HCl from HDA and HCl in the first step is depicted in FIG. 2(A).

In FIG. 2(A), an agitating blade m may take any shape so long as it can uniformly mix a high-viscosity liquid in its entirety and can also form a turbulent zone at least in the vicinity of the agitating blade. The agitating speed may be 2.5 m/sec. or higher, or preferably 4 m/sec. or higher, both in terms of the circumferential velocity (i.e., flow velocity of the reaction mixture along the inner circumferential wall of the reactor). In order to achieve a higher circumferential velocity, it is thus necessary either to enlarge the agitating blade or to increase the revolution speed of the agitating blade.

On the other hand, the smaller the distance between an inlet nozzle a for HCl and another inlet nozzle b for the HDA solution, the better. Accordingly, an HDA inlet tube and an HCl inlet tube may take the form of a double-walled tube so that its outer and inner channels can be used for feeding HDA and HCl respectively. It is necessary to have the openings of the nozzles a,b assume positions in the vicinity of the agitating blade within the turbulent zone so that the HDA solution and HCl are instantaneously mixed and reacted to each other. In this manner, the HDA solution and HCl are continuously fed so as to subject them to the successive salt-forming reaction.

In the above manner, it is possible to obtain an HDA.HCl slurry with a concentration corresponding to the amount of the inert organic solvent used in the above salt-forming step. It is generally possible to obtain a high-quality slurry suited from the viewpoint of handling and reaction readiness upon effecting the subsequent phosgenation, if the concentration of HDA.HCl in the slurry ranges from 10% to 30%.

As an HDA.HCl slurry usable in the phosgenation reaction of this invention, an HDA.HCl slurry obtained in a manner as described above and having a high concentration, usually, within the range of from 10% to 30% may be employed. It should however be borne in mind that its preparation process is not necessarily limited to any specific process. HDA.HCl slurries obtained in accordance with other processes may still be used so long as their viscosities do not impair the practice of the phosgenation reaction.

In the present invention, the phosgenation of the HDA.HCl slurry may be carried out at 120°-190° C., or preferably 130°-170° C. as in usual phosgenation processes. Any temperatures higher than the upper limit result in the formation of more byproducts, while any temperatures lower than the lower limit lead to slower reactions. It is thus impractical to conduct the phosgenation at any temperatures outside the above-described broader range.

The reaction pressure may be above the atmospheric pressure but preferably below 5 kg/cm$^2$G, with the range of 1–3 kg/cm$^2$G being more preferred. Use of a higher pressure is advantageous for the recovery of unreacted phosgene. It is however necessary to increase the degree of excess of phosgene to suppress the occurrence of byproducts under such a higher pressure. As a consequence, such a higher pressure requires a large apparatus for the recovery of phosgene.

Where the reaction pressure is as low as the atmospheric pressure, HDI having a relatively low Cl-HI content can be obtained even when the degree of excess of phosgene is lowered. It is however necessary to additionally provide a freezer or the like besides a condenser in order to recover unreacted phosgene which is discharged from each of the reaction tanks. In the case of a reaction pressure in the neighbourhood of 2 kg/cm$^2$G as generally employed in the process of this invention, such a freezer is not necessary.

The flow rate of phosgene in the phosgenation reaction gives influence to the reaction velocity and the formation of byproducts. If the flow rate of phosgene is low, the reaction proceeds slower and more Cl-HI is produced. It is also necessary to continuously discharge byproduced hydrogen chloride gas, which serves as a raw material for the formation of Cl-HI, from the reaction system by increasing the flow rate of the phosgene to be blown into the reaction tank and hence having the byproduced hydrogen chloride gas blown out of the reaction tank together with the excess phosgene.

Cl-HI and byproduct tar are principally formed from urea which is in turn formed by the reaction between HDA.HCl and resulting HDI. As the reaction proceeds and the HDI concentration increases relative to the concentration of HDA.HCl, the reactions in which urea is formed from the hydrochloride and HDI and Cl-HI and tar are then formed from the urea are allowed to proceed faster compared with the reaction in which HDI is formed from the hydrochloride and phosgene. For this reason, the concentration of unreacted HDA.HCl becomes lower in the latter stage of the reaction compared with its concentration in the feed slurry at the beginning of the reaction. However, the formation of byproducts is promoted if the feed amount of phosgene is decreased in proportion to the number of moles of unreacted HDA.HCl only.

Since the phosgenation reaction of HDA.HCl is very slow, the reaction is usually carried out in two or more stages in view of the volumetric efficiency. In this invention, it is also preferred to divide the reaction into two stages so that HDA.HCl and phosgene are reacted in two stages. In this case, the molar ratio of phosgene to be fed to each of the reaction tanks is determined relative to the total amount of HDA.HCl and HDI in the corresponding reaction mixture. Phosgene, inclusive of unreacted phosgene recirculated to the respective reaction tanks, may be fed in an amount 1-18 molar times or preferably, 5-12 molar times per hour. Where the reaction pressure is high, it is necessary to feed phosgene at a higher molar ratio correspondingly. No substantial changes will however be made to the amount of Cl-HI to be formed even if phosgene is fed in any amounts beyond 18 molar times.

When Cl-HI is contained at a concentration of 2% or higher in the reaction mixture for HDI, HDI is generally lost in an unignorable amount upon separation of Cl-HI. It is thus desirable to lower the concentration a level lower than 2%. The flow rate of phosgene, which is to be blown and fed, can be suitably determined from the reaction pressure and the amount of the liquid reaction mixture so that the content of Cl-HI is adjusted to a desired level.

When the phosgenation reaction is conducted continuously from the salt-forming step, the inert solvent employed in the salt-forming step is introduced, as is, into the phosgenation step. It is hence unnecessary to add any fresh solvent. The solvent is recirculated together with phosgene in the phosgenation reaction and after its recovery, is used again.

When the phosgenation reaction is conducted continuously, it is necessary to place a substantial amount of the solvent in each of the reaction tanks upon starting the phosgenation reaction. It is also required to store the thus-recirculated phosgene in the system prior to charging the HDA.HCl slurry, so that a specific amount of excess phosgene may be blown during the reaction.

In the present invention, it is preferred to conduct the reaction in two steps so that the time of the phosgenation reaction can be shortened. When the continuous reaction is carried out in two steps, it is desirable to control the retention time in such a way that the conversion of HDA.HCl reaches 70-95% in the first stage.

Figure 3:
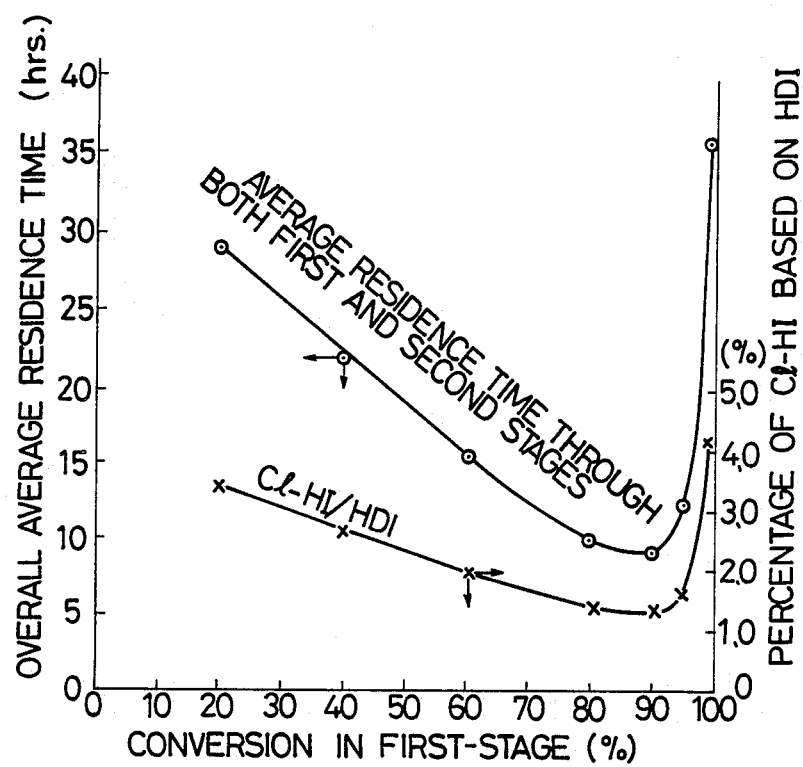
FIG. 3 is a diagrammatic illustration of the relations between the conversion in a first stage and the overall average retention time until completion of the reaction and the proportion of Cl-HI produced in the reaction mixture when the phosgenation reaction of this invention was conducted in two stages.

As understood from FIG. 3, by holding the conversion in the first stage within 70-95%, the whole process can be practiced within a shortest time period, namely, an overall average retention time of about 10-15 hours and the content of the byproduct Cl-HI can also be reduced.

Figure 4:
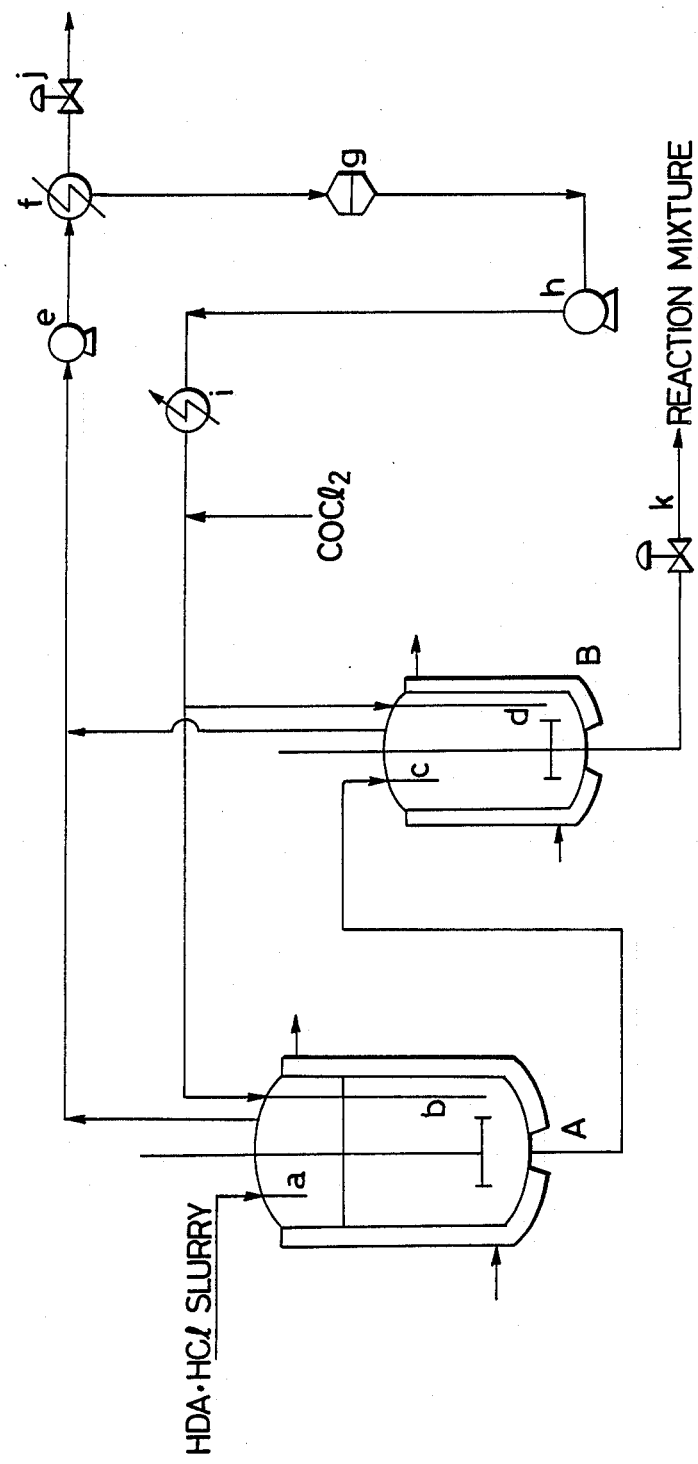
FIG. 4 is an illustrative flow sheet suitable for use in the practice of phosgenation in accordance with this invention.

The two-step process of this invention may preferably be practiced in accordance with the flow sheet of FIG. 4, in which letter a indicates a feed tube of an HDA.HCl slurry (concentration: 10-30%). HDA.HCl is continuously fed together with an inert reaction solvent to the reaction tank in the first stage.

The reaction pressure may preferably be 1-3 kg/cm$^2$G in both first and second stages. The temperature is maintained at 130°-170° C., and the average retention time is set in such a way that the conversion in the first stage reaches 70-95%. Under these conditions, the phosgenation is carried out.

The reaction mixture of the first stage is introduced continuously from a guide tube c into the reaction tank B of the second stage, in which the reaction mixture is phosgenated until the conversion of HDA.HCl reaches 99% or higher.

Phosgene is blown through the nozzles b,d into their corresponding reaction tanks while being controlled by unillustrated flowmeters. Here, phosgene is blown in an amount 1-18 times the number of moles of the sum of HDA.HCl and HDI retained in each of the reaction tanks.

When Cl-HI is contained at a concentration of 2% or higher in the reaction mixture for HDI, HDI is generally lost in an unignorable amount upon separation of Cl-HI. It is thus desirable to lower the concentration a level lower than 2%. The flow rate of phosgene, which is to be blown and fed, can be suitably determined from the reaction pressure and the amount of the reaction mixture so that the content of Cl-HI is adjusted to a desired level.

Since these phosgene streams are recovered and recirculated for their repeated utilization, they generally contain the reaction solvent at substantially high concentrations. Streams of the reaction solvent, which have been discharged from the first and second stages and accompanied by unreacted phosgene and byproduced HCl, are combined together. After compressed in a compressor e, the reaction solvent is cooled in a condenser f so that major portions of the phosgene and reaction solvent are recovered as a liquid mixture at a reservoir g. On the other hand, the byproduced HCl containing a small amount of phosgene is discharged as an off-gas through a pressure reducing valve j.

The thus-recovered phosgene and reaction solvent are pumped up through a pump h and are then combined with a fresh supply of phosgene. The resultant mixture is divided into two portions in accordance with the ratios of phosgene to be blown, said ratios being calculated from the residence times in the first and second stages, and is then fed to the first and second reaction tanks. The mixture of the phosgene and reaction solvent, which is fed in the above manner, may be in the form of a liquid or gas or a mixture thereof. The amount of the fresh supply of phosgene is equal to the amount consumed for the phosgenation (i.e., twice the number of moles of the fed HDA.HCl) plus the amount of the phosgene discharged along with the byproduced HCl.

In the manner mentioned above, the phosgenation reaction is carried out usually over a total residence time of about 10-15 hours. In a usual manner, $N_2$ gas or the like is blown into the reaction mixture which has been continuously drawn out through a discharge line k so that the phosgene gas and solvent are removed from the reaction mixture to obtain HDI in its pure form.

In the purification of HDI by fractionation, the reaction mixture is subjected to a solvent removal step so as to obtain a concentrate which still contains a small amount of the solvent. After removing the tar from the concentrate under reduced pressure, the residue is heat-treated at a temperature close to the boiling point of the remaining solvent and is then subjected to fractionation. In this manner, HDI can be obtained with a high degree of purity while substantially avoiding its coloration.

Examples of this invention will hereinafter be described with reference to FIGS. 2 and 4. In the following Examples, all designations of "part" or "parts" mean part or parts by weight.

EXAMPLE 1

Charged in a salt-forming tank equipped with a jacket for the circulation of cooling water therethrough, which is indicated by letter A in FIG. 2, were 300 parts of o-dichlorobenzene (ODCB). While agitating the ODCB at a circumferential velocity of 6 m/sec., 85 parts (10.62 parts per hour) of HCl gas were blown at room temperature (30° C.) through the nozzle a while controlling the temperature below 60° C. within the system. At the same time, a solution of 123 parts (15.37 parts per hour) of HDA and 500 parts of ODCB was also charged through the nozzle b over 8 hours. Here, the distance between the nozzle a and the nozzle b was 300 mm. The openings of the nozzles a,b are both located at levels 15 mm down from the blade. After the reaction, the liquid reaction mixture, namely, the resulting HDA.HCl slurry had fluidity. Its pH was below 1 and its viscosity was 30,000 cps (at 60° C.). It was substantially free of unreacted HDA.

The thus-obtained 20% slurry of HDA.HCl in ODCB was continuously introduced at a rate of 12 parts (0.013 mole) per hour, by a gear pump l, through the nozzle c, into the first-stage phosgenation reaction tank (capacity: 70 l) designated at letter B in FIG. 2 and equipped with an agitating blade and a steam-circulating jacket. At the same time, 12.5 parts (0.127 mole) of phosgene was introduced through the nozzle d so that HDA.HCl was continuously phosgenated at 150° C. During the phosgenation, unreacted phosgene was cooled down to 30° C. in a condenser e provided above the tank. Thereafter, the thus-cooled unreacted phosgene flew through a separator f, from which it was continuously recycled as a mixture of 25.1 parts (0.254 mole) of liquefied phosgene and 6.16 parts of ODCB to the reaction tank B. On the other hand, hydrogen chloride gas produced in the reaction and a small amount of uncondensed phosgene were caused to flow through a pressure reducing valve k which was adjusted to maintain the inner pressure of the system at 2 kg/cm$^2$G. They were then discharged along with the off-gas which was discharged from the second-stage phosgenation tank C by way of a condenser i and a separator j.

In the above-described manner, HDA.HCl was phosgenated in the reaction tank B for an average residence time of 3.3 hours. The thus-obtained reaction mixture was introduced continuously to the second-stage phosgenation tank (capacity: 150 l) by way of the nozzle g. The first-stage reaction mixture contained 4.15% of phosgene, 3.04% (which corresponds to a conversion of 81.1%) of insoluble matter (unreacted HDA.HCl), 14.3% of HDI, 0.09% (0.6% based on HDI) of Cl-HI and 0.21% of tar.

The first-stage liquid reaction mixture was phosgenated in the second-stage reaction tank C under the same conditions as those employed in the first-stage reaction tank B for an average residence time of 6.9 hours while introducing 12.5 parts (0.127 mole) per hour of phosgene into the second-stage reaction tank C. The resultant second-stage reaction mixture was then taken out of the second-stage reaction tank C. During the phosgenation in both first-stage and second-stage reaction tanks B,C, the molar ratio of phosgene to the fed HDA.HCl was 58.6 times.

The thus-obtained second-stage reaction mixture contained 4.62% of phosgene, 0.03% of insoluble matter, 16.82% of HDI (yield: 96.9%), 0.17% of Cl-HI (1.0% based on HDI) and 0.34% of tar.

In the above-described phosgenation step, ODCB was first of all charged in amounts of 50 parts and 100 parts respectively in the first-stage and second stage reaction tanks. Besides, phosgene was circulated in advance so as to permit blowing of phosgene in desired amounts. After operating the reaction system in the above manner for 10 hours, HDA.HCl was fed to initiate the continuous operation.

EXAMPLE 2

A 20% slurry of HDA.HCl in ODCB, which had been continuously prepared in advance in a usual manner, was continuously introduced at a flow rate of 945.6 parts (1 mole) per hour through a nozzle a into a first-stage phosgenation tank A of FIG. 4. The reaction tank was equipped with an agitating blade and a steam-circulating jacket. At the same time, a mixture of 373.8 parts (37.8 moles) of phosgene in 873.5 parts of ODCB was introduced into and circulated through the first-stage phosgenation tank A so that the phosgenation reaction was continuously carried out at 150° C. and 2 kg/cm$^2$G and with an average residence time of 6.0 hours in the reaction tank A. The resultant liquid reaction mixture was delivered continuously through a guide line c into a second-stage phosgenation tank B.

The first-stage liquid reaction mixture obtained in the above manner contained 4.2% of phosgene, 2.0% of insoluble matter (unreacted HDA.HCl) (conversion 90%), 15.4% of HDI and 0.16% of Cl-HI (1.0% related to HDI).

Then, the first-stage liquid reaction mixture was phosgenated at 150° C. for an average residence time of 3.3 hours in a second-stage reaction tank B while 2056.9 parts (20.8 moles) of phosgene with 496.8 parts of ODCB contained therein, both per hour, were introduced in and circulated through the second-stage reaction tank B. The resulting second-stage reaction mixture was taken out of the second-stage reaction tank B through a discharge line k.

The thus-obtained second-stage reaction mixture contained 4.2% of phosgene, 0.2% of insoluble matter, 16.9% of HDI (yield: 97.0% based on HDA.HCl), and 0.22% of Cl-HI (1.3% based on HDI). Per hour, about 756.5 parts of ODCB were recovered. This corresponded to the amount of ODCB charged as the HDA.HCl slurry.

During the phosgenation step, the byproduced HCl and unreacted phosgene which were discharged from the first-stage and second-stage phosgenation reaction tanks A,B were compressed to 5 kg/cm$^2$G in a compressor e, followed by their cooling to −5° to −10° C. in a condenser f. Thus, a major portion of phosgene with a trace amount of HCl contained therein was recovered together with ODCB in the reservoir g. A major portion of HCl and a small amount of uncondensed phosgene were both discharged through the pressure reducing valve j. The ODCB and phosgene which had been recovered in the reservoir g were heated in a vaporizer i and in a state partially or entirely vaporized, were divided together with the fresh supply of phosgene at the above-described molar ratios and were then charged into the first-stage and second-stage reaction tanks A,B for their reutilization. The amount of the fresh supply of phosgene was equal to the amount of the phosgene consumed per hour in the system plus the amount of the phosgene discharged through the pressure reducing valve j. It was 217.6 parts per hour.

EXAMPLE 3

A reaction was conducted in the same manner as in Example 2 except that the reaction pressure was 5 kg/cm$^2$G and phosgene was brown in amounts of 7399.2 parts (74.8 moles) and 4071.7 parts (41.2 moles) into the first-stage and second-stage reaction tanks respectively.

The thus-obtained first-stage reaction mixture contained 17.0% of phosgene, 1.7% of insoluble matter (conversion: 90%), 13.2% of HDI and 0.15% of Cl-HI (1.1% based on HDI). On the other hand, the second-stage liquid reaction mixture contained 17.1% of phosgene, 0.2% of insoluble matter, 14.3% of HDI and 0.25% of Cl-HI (1.7% based on HDI).

In the present Example, the unreacted phosgene, byproduced HCl and accompanying ODCB which had been discharged from the first-stage and second-stage reaction tanks A,B were combined together as they were, namely, without causing them to flow through the compressor e. The resultant mixture was cooled to −5° to −10° C. in the condenser f. In this Example, the amount of the fresh supply of phosgene was 242.9 parts.

EXAMPLE 4

In exactly the same manner as in Example 1, 1,000 parts of a 20% slurry of HDA.HCl in ODCB were obtained. Then, 1,000 parts of ODCB were added to the slurry to dilute the HDA.HCl concentration to 10%.

Then, 1,000 parts (0.53 mole) of the above-diluted slurry of HDA.HCl were charged in a reaction tank equipped with an agitating blade, reflux condenser and steam-circulating jacket. While vigorously agitating the slurry and charging phosgene at a flow rate of 76 parts (0.41 mole) per hour, the HDA.HCl was phosgenated at 150° C. and 0.5 kg/cm$^2$G for 12 hours.

The thus-obtained reaction mixture contained 1.2% of phosgene, 0.07% of insoluble matter, 8.7% of HDI (yield: 96.0%), 0.06% of Cl-HI (0.7% based on HDI) and 0.25% of tar.

COMPARATIVE EXAMPLE 1

Eight hundred parts of ODCB and 123 parts of HDA were charged in a reactor similar to that employed in Example 1, into which 85 parts of HCl gas were blown to convert the HDA into its hydrochloride. When the charging of the HCl gas had been completed, the reaction mixture was allowed to flow only in the vicinity of the agitating blade. In the non-flowing zone, its pH was above 9. Thereafter, 85 parts of HCl gas were additionally blown over 4 hours. However, some non-flowing zones still remained in the reactor. In each of these zones, the pH was above 9 and the viscosity was 70,000 cps.

Thereafter, 1,000 parts of ODCB were added to 1,000 parts of the above-obtained HDA.HCl slurry to adjust the concentration of HDA.HCl to 10%.

In exactly the same manner as in Example 4, 1,000 parts (0.53 moles) of the above-diluted slurry were phosgenated. The resulting reaction mixture contained 1.2% of phosgene, 0.15% of insoluble matter, 7.72% of HDI (yield: 86.0%), 0.47% of Cl-HI (6.1% based on HDI) and 0.67% of tar.

What is claimed is:

1. Process for preparing hexamethylene diisocyanate, which comprises:
    charging a slurry of hexamethylenediamine hydrochloride in an inert organic solvent into the first of two stages, each composed of a tank-shaped reactor which are maintained under a pressure above atmospheric pressure and below 3 kg/cm$^2$G;
    controlling the conversion of hexamethylenediamine hydrochloride into hexamethylene diisocyanate in the first stage within the range of from 70 to 95 percent;
    subjecting the slurry to a phosgenation reaction by controlling the amount of phosgene at a level which is 5 to 12 molar times per hour the total amount of hexamethylenediamine hydrochloride and hexamethylene diisocyanate in the corresponding reaction mixture;
    exhausting unreacted phosgene which contains byproduced HCl; said unreacted phosgene being recycled after separating said HCl; and
    controlling the overall residence time in the phosgenation reaction at from 9 to 15 hours and the reaction temperature at from 130° to 170° C.

* * * * *